United States Patent [19]
Darsow

[11] Patent Number: 5,872,276
[45] Date of Patent: *Feb. 16, 1999

[54] PROCESS FOR PREPARING DIALKYL SUCCINATES

[75] Inventor: Gerhard Darsow, Krefeld, Germany

[73] Assignee: Bayer Aktiengesellschaft, Leverkusen, Germany

[*] Notice: The term of this patent shall not extend beyond the expiration date of Pat. No. 5,606,099.

[21] Appl. No.: 964,565

[22] Filed: Nov. 5, 1997

[30] Foreign Application Priority Data

Nov. 25, 1996 [DE] Germany .................. 196 48 761.7

[51] Int. Cl.⁶ .................................................. C07C 69/34
[52] U.S. Cl. ........................................... 560/190; 554/121
[58] Field of Search .............................. 560/190; 554/121

[56] References Cited

U.S. PATENT DOCUMENTS 5,606,099 2/1997 Darsow .................................... 560/190

FOREIGN PATENT DOCUMENTS

| | | |
|---|---|---|
| 0190424 | 8/1986 | European Pat. Off. . |
| 0728731 | 8/1996 | European Pat. Off. ...... C07C 67/303 |
| 3503485 | 8/1986 | Germany . |

*Primary Examiner*—Samuel Barts
*Attorney, Agent, or Firm*—Sprung Kramer Schaefer & Briscoe

[57] ABSTRACT

Dialkyl maleates can be hydrogenated with hydrogen in a catalytic liquid-phase hydrogenation to give dialkyl succinates, wherein the hydrogenation is carried out continuously at a pressure of from 50 to 400 bar and a reaction temperature of from 30 to 160° C. over a fixed bed of oxygen-free and support-free shaped bodies comprising pressed powders of the elements of the iron subgroup of transition group VIII of the Periodic Table of the Elements (Mendeleev) or their alloys or mixtures with one another with additions of elements of transition groups IV and/or V; hydrogenation-inert elements can additionally be present. The shaped bodies have a compressive strength of from 20 to 220N and an internal surface area of from 10 to 100 m²/g.

13 Claims, No Drawings

PROCESS FOR PREPARING DIALKYL SUCCINATES

BACKGROUND OF THE INVENTION

1. Field of the Invention

The present invention relates to an inexpensive, continuous process for preparing dialkyl succinates in particularly high yields from dialkyl maleates, in which only very small amounts of the 1,4-butanediol usually produced in the hydrogenation of maleic esters and no monocarboxylic and no hydroxycarboxylic acids having <4 carbon atoms are formed.

Dialkyl sbuccinates are important, readily biodegradable solvents for surface coatings and plasticizers for thermoplastic polyesters having particular mechanical and chemical properties.

2. Description of the Related Art

It is known that dialkyl succinates can be prepared by esterification of succinic acid or succinic anhydride with the corresponding monoalcohols, with acid components frequently being used as esterification catalysts and high alcohol excesses being employed. It is also known that dialkyl maleates can be hydrogenated batchwise with hydrogen in a suspension process using a pulverulent $Pd/Al_2O_3$ catalyst to give the corresponding dialkyl succinates (EP 190 424). The course of the reaction can be shown by the following reaction scheme:

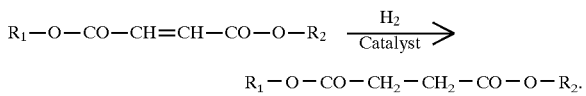

Here, $R_1$ and $R_2$ can be identical or different n- or iso-alkyl radicals having from 1 to 12 carbon atoms or cyclic alkyl radicals having from 3 to 6 carbon atoms.

Batchwise processes have the disadvantage that their capacity relative to the reaction volume is very small and thus large reaction apparatuses and storage tanks are needed. Energy consumption and personnel requirements are relatively high. Continuous powder catalyst processes which employ a plurality of hydrogenation reactors connected in a cascade avoid some of these disadvantages.

However, it is still necessary for the pulverulent catalysts to be repeatedly and precisely metered in, pumped around and quantitatively filtered off from the reaction product. The catalyst slurry pumps are subject to high mechanical wear. The quantitative removal of the pulverulent catalysts from the reaction product is costly. Furthermore, there is a great danger of the catalyst activity being reduced relatively quickly by the additional operations, so that high catalyst consumptions have to be expected. It is therefore advantageous to allow the reaction to proceed over fixed-bed catalysts. Such catalysts have to have a high activity which must not decrease over a prolonged period of time because frequent catalyst replacements in fixed-bed reactions are likewise costly. In addition, there is always a desire to achieve particularly high catalyst conversions (g of dialkyt maleate/l of catalyst * h).

SUMMARY OF THE INVENTION

It has now surprisingly been found that dialkyl maleates can be hydrogenated continuously in particularly high yields over a fixed bed of support-free shaped bodies comprising oxygen-free metal powders of one or more elements of the iron subgroup of transition group VIII of the Periodic Table (Mendeleev) alloyed with one or more elements of transition groups IV and/or V of the Periodic Table to give the corresponding dialkyl succinates. The powders used can further comprise proportions of elements which are not catalytically active (e.g. silicon, aluminum, carbon) without the high activity being reduced. The solids have to have a compressive strength of from 20 to 220N and an internal surface area of from 10 to 100 $m^2/g$.

Preference is given to using dialkyl maleates having a purity of $\geq 99\%$. However, dialkyl maleates having a lower purity can also be reacted virtually quantitatively.

The invention accordingly provides a process for the continuous preparation of dialkyl succinates of the formula

where $R^1$ and $R^2$ are, independently of one another, straight-chain or branched $C_1$–$C_{12}$-alkyl or $C_3$–$C_6$-cycloalkyl, $R^3$ represents hydrogen, chlorine or straight-chain or branched $C_1$–$C_{12}$-alkyl and $R^4$ is hydrogen or straight-chain or branched $C_1$–$C_4$-alkyl, by catalytic hydrogenation of dialkyl maleates or fumarates of the formula

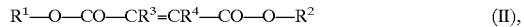

where $R^1$, $R^2$, $R^3$ and $R^4$ are as defined above, which comprises carrying out the hydrogenation in the liquid phase at an $H_2$ pressure of from 50 to 400 bar using a 20- to 60-fold molar amount of $H_2$, based on the stoichiometric amount, and at a temperature of from 30° to 160° C. over a fixed bed of oxygen-free and support-free catalysts which are in the form of pressed shaped bodies having a compressive strength of from 20 to 220N and an internal surface area of from 10 to 100 $m^2/g$ produced from metal powders comprising at least 50% by weight of one or more elements of the iron group of the Periodic Table of the Elements (Mendeleev) alloyed with at least 6% by weight of one or more elements of transition groups IV and/or V and from 0 to 20% by weight of one or more hydrogenation-inert elements selected from the group consisting of aluminum, silicon and carbon, all based on the total weight of the metal powder.

DETAILED DESCRIPTION OF THE INVENTION

The compressive strength of the support-free shaped bodies can be determined in accordance with DIN 50106. Support-free shaped bodies can be checked for the internal surface areas in accordance with the claims and thus for usability in the process of the invention by methods which have been described by F. M. Nelsen and F. T. Eggertsen, Analyt. Chem.30 (1958), pp. 1387–1390 or S. J. Gregg and K. S. W. Sing, Adsorption, Surface Area and Porosity, London 1982, Chapters 2 and 6.

The iron group of transition group VIII of the Periodic Table (Mendeleev) consists of the elements iron, cobalt and nickel. The support-free shaped bodies to be used according to the invention comprise one or more of these elements in amounts of at least 50% by weight, preferably at least 60% by weight, in particular at least 65% by weight, based on the total weight of the support-free shaped bodies.

Transition group IV of the Periodic Table consists of the elements titanium, zirconium and hafnium. Transition group V of the Periodic Table consists of the elements vanadium, niobium and tantalum. The support-free shaped bodies to be used according to the invention comprise one or more of these elements in amounts of at least 6.0% by weight, preferably at least 7.5% by weight, in particular at least 9.0% by weight, based on support-free shaped bodies; they comprise one or more of these elements in amounts of at most 30% by weight, preferably at most 20% by weight and in particular at most 15% by weight, based on the total weight of the support-free shaped bodies.

The support-free shaped bodies to be used according to the invention may further comprise, in each case based on the total weight of the support-free shaped bodies, up to 20% by weight, preferably up to 15% by weight, of other elements; examples of such elements which are not catalytically active include aluminum, silicon and carbon. According to a preferred embodiment, the support-free shaped bodies comprise, apart from the metals of transition groups VIII, IV and/or V, not more than 15% by weight of aluminum and not more than 5% by weight of other elements among the hydrogenation-inert elements mentioned.

The support-free shaped bodies can be produced according to customary methods by pressing the metal powders on tabletting and pelletizing machines under high pressure. To improve the adhesion of the metal particles, it is also possible to use graphite in amounts of from 0.5 to 1.5% by weight, based on the total weight of the constituents forming the catalyst, or adhesives in small amounts. The support-free shaped bodies are preferably produced in an oxygen-free atmosphere in order to avoid surface oxidation. Shaped bodies which are most effective and most favorable for carrying out the reaction are tableted and pelletized shaped bodies in the form of spheres or cylinders having diameters of from 3 to 7 mm. A factor which is of considerable importance is the compressive strength of the shaped bodies which according to the invention is from 20 to 220N, preferably from 70 to 140N. Lower compressive strengths lead to disintegration of the shaped body or to erosive abrasion which would cause metal contamination of the reaction product. Higher values require a disproportionate outlay for pressing without further advantages being achieved. Another factor of considerable importance is the internal surface area of the shaped bodies which according to the invention is from 10 to 100 m$^2$/g and is decisive for a very quantitative conversion of the starting materials. Macroscopically, the shaped bodies have a smooth surface.

The hydrogenation process is carried out using precompressed pure hydrogen at a pressure of from 50 to 400 bar, preferably from 100 to 300 bar, in a 20- to 60-fold, preferably 20- to 40-fold, molar amount, based on the stoichiometric amount.

The hydrogenation process is carried out at temperatures of from 30 to 160° C, preferably from 40° to 100° C. Lower temperatures require higher residence times or acceptance of a less than quantitative conversion. Higher temperatures lead to formation of 1,4-butanediol and ester alcohol as by-products.

The weight hourly space velocity over the catalyst can be from 600 to 1500 g of dialkyl maleate/l of catalyst-h.

The hydrogenation is carried out continuously by the fixed-bed method over the support-free shaped bodies of the type described serving as hydrogenation catalysts by allowing the liquid dialkyl maleates to be hydrogenated to flow in cocurrent with the previously mixed-in hydrogen from the bottom upward over the shaped bodies placed in the hydrogenation reactor or by feeding them in from the bottom in a direction opposite to the hydrogen flowing in from the top countercurrent process).

The process of the invention can naturally also be carried out in solvents. Suitable solvents which are inert under the reaction conditions are, for example, di-n-propyl ether, diisopropyl ether, di-n-butyl ether, tetrahydrofuran, dioxane and γ-butyrolactone. The process can also be carried out in the presence of the dialkyl succinate to be formed.

The hydrogenation reactor can be either a single high-pressure tube of steel or a steel alloy which is completely or partly filled with the support-free shaped bodies, where arrangement on trays (wire baskets or the like) can also be useful, or else an unjacketed high-pressure tube bundle whose individual tubes are completely or partly filled with shaped bodies.

Under the reaction conditions indicated, quite unexpectedly high catalyst lives of 15,000 hours and more can be achieved in this way, which leads to catalyst consumptions of <0.05% by weight, based on reaction product produced; such low catalyst consumptions have hitherto not been able to be achieved in the hydrogenation of maleic esters.

The reaction mixture leaving the hydrogenation reactor is depressurized; it is here possible to collect the excess hydrogen and, after compression and replacement of hydrogen consumed, to reuse it. At a conversion of from 99.9 to 100%, the reaction mixture comprises at least 90% by weight of dialkyl succinates.

Unlike support-containing catalysts, the oxygen-free and support-free fixed-bed catalysts to be used according to the invention do not tend to undergo "bleeding", i.e. there is no tendency for migration of catalyst constituents in ionic or colloidal form into the solution phase of the substrate, so that the substrate is not contaminated by heavy metals which normally can be removed from the substrate only with difficulty, for example by means of ion exchangers. The catalyst metals to be used can, for instance after prolonged use of the catalyst, be easily worked up and reused since the heavy metals do not have to be laboriously separated from a support material.

Starting materials to be used according to the invention are dialkyl maleates or fumarates of the formula (II) above. Straight-chain or branched $C_1$–$C_{12}$-alkyl is here methyl, ethyl, propyl, i-propyl, butyl, i-butyl, pentyl, i-pentyl, hexyl, i-hexyl or a subsequent n- or i-homologue having 7, 8, 9, 10, 11 or 12 carbon atoms. $C_3$–$C_6$-Cycloalkyl is here cyclopropyl, methyl-cyclopropyl, dimethyl-cyclopropyl, cyclobutyl, cyclopentyl, methyl-cyclopentyl or cyclohexyl. $R^3$ is preferably the radical $R^{13}$ which is hydrogen or straight-chain or branched $C_1$–$C_{12}$-alkyl, particularly preferably the radical $R^{23}$ which is hydrogen or methyl.

Furthermore, $R^4$ is preferably the radical $R^{14}$ which is hydrogen or methyl.

Furthermore, the starting materials of the formula (II) are preferably dialkyl maleates in which the radicals $R^1$, $R^2$, $R^3$ and $R^4$ are as defined above.

Furthermore, $R^1$ and $R^2$ are preferably the radicals $R^{11}$ and $R^{12}$ which are, independently of one another, straight-chain or branched $C_1$–$C_6$-alkyl, cyclopropyl or cyclohexyl. Furthermore, the starting materials of the formula (I) are preferably dialkyl maleates which are not substituted at the C—C double bond and in which the radicals $R^1$ and $R^2$ are as defined above.

The dialkyl succinates produced are, after distillative removal of a small first low-boiler fraction and possibly a high-boiler fraction, obtained in a purity of ≧99.9% by weight and in this quality can be used for all further processes.

EXAMPLES

Example 1

An upright, thermally insulated high-pressure tube made of stainless steel and having an internal diameter of 45 mm and a length of 1 m was charged with 1.4 l of a hydrogenation catalyst which had been produced by tableting a metal powder of an Ni/Zr alloy having a Zr content of 14.9% by weight and an additional Al content of 10.5% by weight and had a cylinder height of 5 mm, a diameter of 5 mm, a compressive strength of 75N on the cylindrical surface and an internal surface area of 81 m²/g. 1000 g/h of dimethyl maleate (purity ≧99.5% by weight) together with the 20-fold molar amount of high-purity hydrogen under a pressure of 300 bar were pumped through this tube from the bottom upward. Dimethyl maleate and hydrogen were first passed together through a heat exchanger and thus heated so that they entered the high-pressure tube at a temperature of 60° C. The mixture of liquid reaction product and excess hydrogen leaving the high-pressure tube was conveyed to a separator from which the hydrogen, after replacement of the amount consumed, was again pumped together with fresh dimethyl maleate into the preheater and from there again into the high-pressure tube. The colorless and clear liquid of the reaction product was, after depressurization to atmospheric pressure and cooling, analyzed by gas chromatography. Alcohol by-products present were 0.2% by weight of methanol and 0.1% by weight of 1,4-butanediol. The dimethyl maleate content of the organic reaction product was <0.1% by weight, so that the dimethyl succinate content was >99.5% by weight. The dimethyl succinate produced was, after removal of the secondary constituents by distillation, obtained in a purity of 99.9% by weight and had a boiling point of 196° C. The catalyst had an unchanged activity after a running time of 1620 hours.

Example 2

In a high-pressure tube as in Example 1 and at a temperature of 45° C. and a hydrogen pressure of 200 bar, the hydrogen was, in reversed reaction flow compared with Example 1, fed in countercurrent to the rising dimethyl maleate, with the same amount per hour as in Example 1 being hydrogenated. The catalyst had been-produced by tableting a pulverized Ni/Fe/Zr alloy. The alloy had an iron content in nickel of 5% by weight and a Zr content of 10.9% by weight. The pellets had a cylinder height of 5 mm, a diameter of 5 mm, a compressive strength of 107N on the cylindrical surface and an internal surface area of 93 m²/g. After a running time of 2100 hours, the conversion of the dimethyl maleate used was 99.95% by weight. The methanol content of the reaction product was 0.2% by weight and the 1,4-butanediol content was 0.1% by weight, so that the dimethyl succinate content of the reaction product was >99.6% by weight. After removal of the impurities by distillation, the dimethyl succinate produced was obtained in a purity of 99.9% by weight.

Example 3

An upright, thermally insulated high-pressure tube of stainless steel having an internal diameter of 45 mm and a length of 1 m was charged with 1.4 l of a hydrogenation catalyst which had been produced by tableting powder of a Ni/Zr/V alloy having a Zr content of 10.9% by weight, a V content of 9.2% by weight and an additional Al content of 10.1% by weight and had a cylinder height of 5 mm, a diameter of 5 mm, a compressive strength of 109N on the cylindrical surface and an internal surface area of 81 m²/g. 1200 g/h of diethyl maleate together with the 30-fold molar amount of high-purity hydrogen under a pressure of 300 bar were pumped through this tube from the bottom upward. Before entering the high-pressure tube, the diethyl maleate and hydrogen were brought to a temperature of 60° C. After a running time of 1120 hours, the conversion of the diethyl maleate used was 100% by weight. The ethanol content of the reaction product was 0.4% by weight and the 1,4-butanediol content was 0.1% by weight, so that the diethyl succinate content was 99.5% by weight. After removing the impurities by distillation, the diethyl succinate produced was obtained in a purity of 99.9% by weight. It had a boiling point of 217° C.

Example 4

In a high-pressure tube as in Example 3 and at a temperature of 85° C. and a hydrogen pressure of 200 bar, the same amount of diethyl maleate per hour was hydrogenated. The catalyst was produced by tableting a pulverized Ni/Zr/Al alloy. The alloy had a Zr content in Ni of 14.9% by weight and an Al content of 10.5% by weight. The pellets had a cylinder height of 5 mm, a diameter of 5 mm, a compressive strength of 75N on the cylindrical surface and an internal surface area of 81 m²/g. After a running time of 1200 hours, the conversion of the diethyl maleate used was 99.9% by weight. The ethanol content of the reaction product was 0.3% by weight and the 1,4-butanediol content was 0.1% by weight, so that the diethyl succinate content of the reaction product was 99.5% by weight.

Example 5

In a high-pressure tube as in Example 1, but of high-pressure steel N 9, 1200 g/h of di-n-butyl maleate were hydrogenated at a temperature of 90° C. and a hydrogen pressure of 300 bar. The catalyst was produced by tableting powder of an Ni/Zr/Al alloy having a Zr content of 14.9% by weight and an Al content of 10.5% by weight. The pellets had a cylinder height of 5 mm, a diameter of 5 mm, a compressive strength of 75N and an internal surface area of 81 m²/g. After a running time of 2100 hours, the di-n-butyl succinate content of the reaction product was 99.5% by weight. After removal of the impurities by distillation, the di-n-butyl succinate produced was obtained in a purity of 99.9% by weight (Bp$_4$: 108° C.).

Example 6

In a high-pressure tube as in Example 1, 850 g/h of di-n-propyl maleate were hydrogenated at a temperature of 65° C. and a hydrogen pressure of 200 bar. The catalyst was obtained by tableting a pulverized Ni/V/Si/Al alloy having a V content of 9.2% by weight, an Si content of 2.8% by weight and an Al content of 9.8% by weight. The pellets had a cylinder height of 5 mm, a diameter of 5 mm, a compressive strength of 104N and an internal surface area of 95 m²/g. After a running time of 1100 hours, the conversion of the di-n-propyl maleate used was ≧99.5% by weight. The n-propanol content of the reaction product was 0.3% by weight and 1,4-butanediol content was 0.18% by weight, so that the di-n-propyl succinate content was ≧99.5% by weight. After distillation of the crude di-n-propyl succinate, this had a boiling point of 248° C.

What is claimed is:

1. A process for the continuous preparation of a dialkyl succinate of the formula

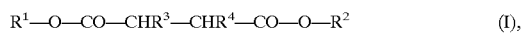

$$R^1\text{—}O\text{—}CO\text{—}CHR^3\text{—}CHR^4\text{—}CO\text{—}O\text{—}R^2 \qquad (I),$$

where
$R^1$ and $R^2$ are, independently of one another, straight-chain or branched $C_{1-C_{12}}$-alkyl or $C_3\text{–}C_6$-cycloalkyl, $R^3$ represents hydrogen, chlorine or straight-chain or branched $C_1$–$C_{12}$-alkyl and $R^4$ is hydrogen or straight-chain or branched $C_1$–$C_4$-alkyl, by catalytic hydrogenation of a dialkyl maleate or fumarate of the formula

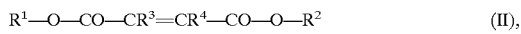

$$R^1\text{—}O\text{—}CO\text{—}CR^3\text{=}CR^4\text{—}CO\text{—}O\text{—}R^2 \qquad (II),$$

where $R^1$, $R^2$, $R^3$ and $R^4$ are as defined above, which comprises carrying out the hydrogenation in the liquid phase at an $H_2$ pressure of from 50 to 400 bar using a 20- to 60-fold molar amount of $H_2$, based on the stoichiometric amount, and at a temperature of from 30° to 160° C. over a fixed bed of an oxygen-free and support-free catalyst which is in the form of pressed shaped bodies having a compressive strength of from 20 to 220N and an internal surface area of from 10 to 100 m$^2$/g produced from metal powders comprising at least 50% by weight of one or more elements of the iron group of the Periodic Table of the Elements (Mendeleev) alloyed with at least 6.0% by weight of one or more elements of transition groups IV and V and from 0 to 20% by weight of one or more hydrogenation-inert elements selected from the group consisting of aluminum, silicon and carbon, all based on the total weight of the metal powder.

2. The process of claim 1, wherein the metal powders comprise at least 60% by weight of one or more elements of the iron group of transition group VIII of the Periodic Table (Mendeleev).

3. The process of claim 2, wherein the metal powders comprise at least 65% by weight of one or more elements of the iron group of transition group VIII of the Periodic Table (Mendeleev).

4. The process of claim 1, wherein the metal powders have a content of at least 7.5% by weight but no more than 30% by weight of elements of transition groups IV and V of the Periodic Table (Mandeleev).

5. The process of claim 4, wherein the metal powders have a content of at least 9% by weight of elements of transition groups IV and V.

6. The process of claim 4, wherein the metal powders have a content of at most 20% by weight of elements of transition groups IV and V.

7. The process of claim 6, wherein the metal powders have a content of at most 15% by weight of elements of transition groups IV and V.

8. The process of claim 1, wherein the metal powders have, when hydrogenation-inert elements are present, a content of from 0 to 15% by weight of aluminum and from 0 to 5% by weight of other hydrogenation-inert elements.

9. The process of claim 1, wherein the shaped bodies have a compressive strength of from 70 to 140N.

10. The process of claim 1, wherein the shaped bodies have a cylindrical or spherical shape and diameters of from 3 to 7 mm.

11. The process of claim 1, wherein the hydrogenation is carried out at an $H_2$ pressure of from 100 to 300 bar.

12. The process of claim 1, carried out in the presence of a 20- to 40-fold molar amount of $H_2$, based on the stoichiometric amount.

13. The process of claim 1, wherein the dialkyl maleate to be hydrogenated passes through the hydrogenation reactor from the bottom upward while the hydrogen required for the hydrogenation is either pumped into the reactor together with the ester or is fed in countercurrent to the latter, flowing from the top downward.

* * * * *

UNITED STATES PATENT AND TRADEMARK OFFICE
CERTIFICATE OF CORRECTION

PATENT NO. : 5,872,276
DATED : February 16, 1999
INVENTOR(S) : Darsow

It is certified that error appears in the above-indentified patent and that said Letters Patent is hereby corrected as shown below:

Col. 6, Line 67    Delete "$C_{12}$" after "$C_1$-" and before "-alkyl" and substitute --$C_{12}$--

Col. 8, Line 2    Delete "Mandeleev" and substitute --Mendeleev--

Signed and Sealed this

Twenty-third Day of November, 1999

Attest:

Q. TODD DICKINSON

Attesting Officer    Acting Commissioner of Patents and Trademarks